Oct. 6, 1953 W. KORDES Plant Pat. 1,219
ROSE PLANT
Filed Sept. 30, 1952
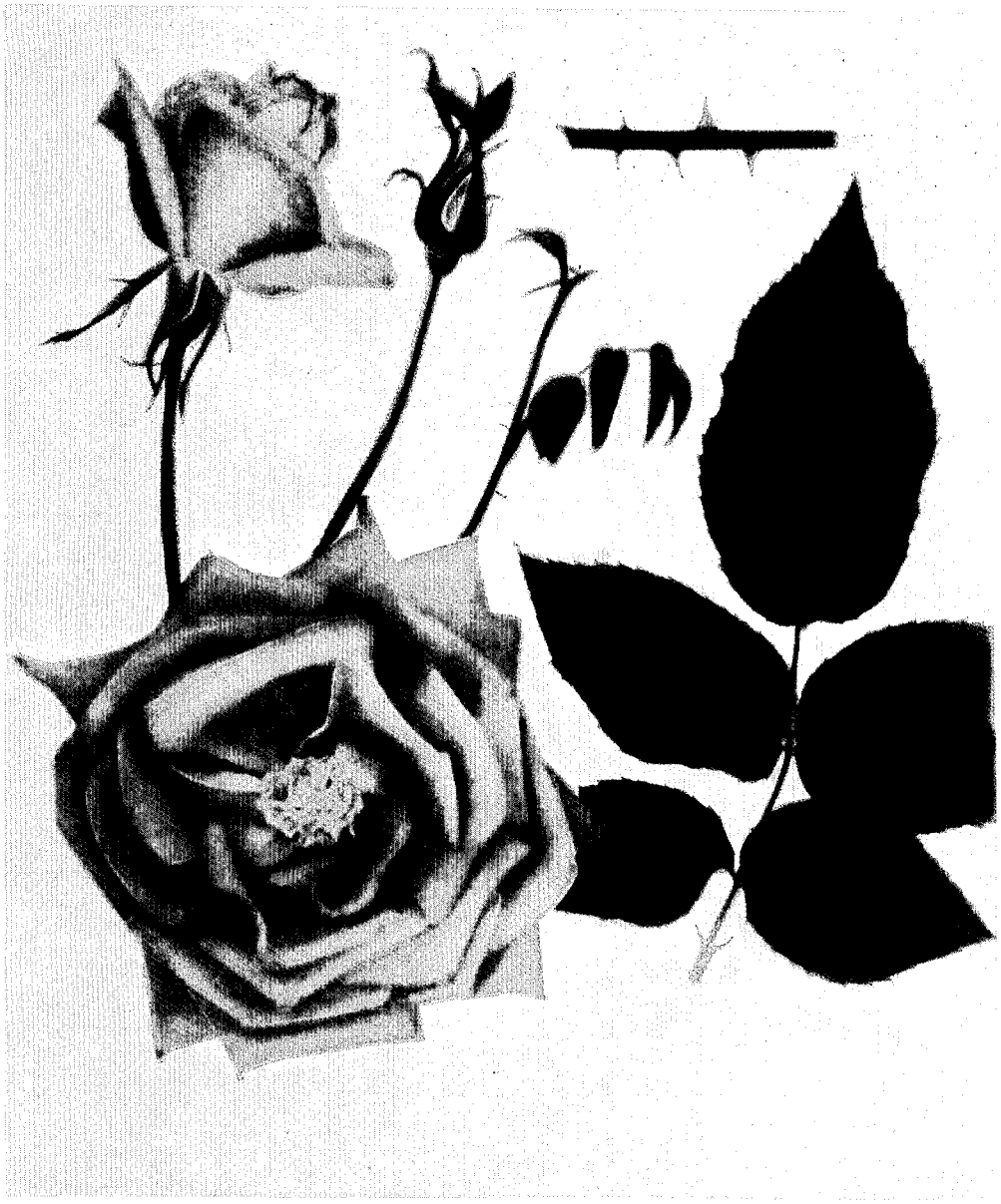
Inventor.
Wilhelm Kordes
By: Robbins Robb
Attorneys.

Patented Oct. 6, 1953

Plant Pat. 1,219

UNITED STATES PATENT OFFICE 1,219

ROSE PLANT

Wilhelm Kordes, Holstein, Germany, assignor to Jackson & Perkins Company, Newark, N. Y., a corporation of New York Application September 30, 1952, Serial No. 312,424

1 Claim. (Cl. 47—61)

The present invention relates to a new and distinct variety of rose plant of the hybrid tea class, which was originated by me by crossing the variety "Poinsettia" (unpatented) with the variety "Crimson Glory" (Plant Patent No. 105).

The primary objective in making this cross was to create a new variety of red rose having the vigor and growth of the variety commercially known as "Poinsettia," and which bears blooms of a color and fragrance comparable to those of the variety commercially known as "Crimson Glory." This objective was fully achieved, as evidenced by the following unique combination of dominant characteristics which distinguish my new variety from each of its parents, as well as from all other varieties of its class:

(1) The vigorous growth and attractive foliage of the plants;

(2) The hooded form of the buds which is maintained and enhances the attractiveness of the buds until the buds open;

(3) The Carmine general color tonality of the flowers, and their lightly overcast Spectrum Red shading, which is a combination of the color characteristics of the two parent varieties; and (4) The single white-striped petal which usually occurs in the middle of each flower and constitutes a prominent and unique characteristic thereof.

Asexual reproduction of my new variety by budding at Newark, New York, and also at Pleasanton, California, U. S. A., shows that the foregoing characteristics and distinctions come true to form and are established and transmitted through succeeding propagations.

The accompanying drawing shows specimens of the foliage, stems, thorns and flowers of my new variety, with the foliage and flowers shown in different stages of development.

The following is a detailed description of the new variety, with color terminology in accordance with Ridgway's Color Standards and Nomenclature:

Parentage: Seedling.
*Seed parent.*—"Poinsettia."
*Pollen parent.*—"Crimson Glory."
Classification:
*Botanic.*—Hybrid tea.
*Commercial.*—Hybrid tea.

*Flower*

(Observations made in the fields at Newark, New York, U. S. A., during the latter part of the month of June and at about mid-morning.)

Blooming habit: Recurrent—continuous.
Bud:
*Size.*—Large.
*Form.*—Long-pointed; is not affected by wet or hot weather.
*Color.*—When sepals first divide—Oxblood Red, Plate 1. When petals begin to unfurl—Carmine, Plate 1, overcast with Spectrum Red, Plate 1. When half blown: inside of petals—Carmine, Plate 1, slightly overcast with Spectrum Red, Plate 1; reverse of petals—Carmine, Plate 1.
*Sepals.*—Branched; "hood" above bud; curl back when petals begin to unfurl. Color: inside—Deep Turtle Green, Plate 32; outside—Dark Dull Yellow-Green, Plate 32. Tip end on inside and outside of sepal lightly overcast with Garnet Brown, Plate 1.
*Calyx.*—Color—Spinach Green, Plate 5. Shape — pear. Size — large. Aspect—smooth. Odor when rubbed—none.
*Peduncle.* — Length — medium. Aspect—prickly. Color—Grass Green, Plate 6. Strength—erect; heavy.
*Opening.*—Opens up well; is not affected by adverse weather conditions.
Bloom:
*Size.*—Large. Average size when fully expanded—5½ inches.
*Borne.*—Singly and several together.
*Stems.*—Long; strong.
*Form.*—When first open—cupped; high center. Permanence—retains its form to the end.
*Petalage.*—Double (full but open center). Number of petals under normal conditions—22 to 25.
*Color.*—Center of flower—Carmine, Plate 1, lightly overcast with Spectrum Red, Plate 1. Outer petals—Carmine, Plate 1, lightly overcast with Pomegranate Purple, Plate 12. Base of petals (aiglet)—Primrose Yellow, Plate 30. Inside of petals—Carmine, Plate 1, overcast with Spectrum Red, Plate 1. Reverse of petals—Carmine, Plate 1, lightly overcast with Pomegranate Purple, Plate 12. General tonality from a distance—Carmine, Plate 1, overcast with Spectrum Red, Plate 1.
*Variegations.*—One petal in the middle of the flower striped in White, Plate 53.
*Discoloration.*—General tonality at end of first day—Carmine, Plate 1, lightly overcast with Spectrum Red, Plate 1. Second day—Carmine, Plate 1, overcast with Spectrum Red, Plate 1. Third day—Carmine, Plate 1, overcast with Pomegranate Purple, Plate 12.

Petals:

*Texture.*—Thick; is not affected by wet or hot weather.

*Appearance.*—Inside—velvety; outside—satiny.

*Form.*—Oval.

*Arrangement.*—Imbricated (regularly arranged shingle-like).

*Petaloids in center.*—Few; large.

*Persistence.*—Drop off cleanly.

*Fragrance.*—Moderate. Nature—tea (average hybrid tea scent).

*Lasting quality.*—On the plant and as cut flower—long.

*Genital organs*

Stamens, anthers: Large; many.

*Color.*—Salmon Orange, Plate 2.

*Arrangement.*—Regular around styles.

Stamens, filaments (threads):

*Length.*—Long.

*Color.*—Scarlet Red, Plate 1.

Pollen: Color—Bittersweet Pink, Plate 2.

Styles: Columnar; uneven length; medium length; thin.

Stigmas: Color—Pale Yellow Orange, Plate 3.

Ovaries: All enclosed in calyx.

Seeds: None.

*Plant*

Form: Bush.

Growth: Vigorous; upright.

Foliage: 5 to 7 leaflets.

*Size.*—Large.

*Quantity.*—Abundant.

*Color.*—New foliage: upper side—Yellowish Oil Green, Plate 5, lightly overcast with Nopal Red, Plate 1; under side—Courge Green, Plate 17, lightly overcast with Nopal Red, Plate 1. Old foliage: upper side—Dark Dull Yellow-Green, Plate 32; serrations—Garnet Brown, Plate 1; under side—Light Elm Green, Plate 17.

*Shape.*—Oval pointed.

*Texture.*—Upper side and under side—smooth. Ribs and veins—ordinary.

*Edge.*—Serrated (saw-toothed).

*Serration.*—Single; small.

*Leaf stem.*—Color—Carmine, Plate 1. Under side—prickles.

*Stipules.*—Medium length; bearded.

Wood:

*New wood.*—Color—Yellowish Oil Green, Plate 5. Bark—smooth.

*Old wood.*—Color—Yew Green, Plate 31. Bark—smooth.

Thorns:

*Thorns.*—Quantity—on main stalks from base and on laterals from stalk—ordinary. Form—flat base; medium length; straight and hooked downward. Color when young—Eugenia Red, Plate 13. Position—irregular.

*Prickles and short needles.*—On main stalks and on laterals—none.

I claim:

A new and distinct variety of rose plant of the hybrid tea class, characterized particularly as to novelty by the vigorous growth and attractive foliage of the plant, by the moderate tea fragrance of its flowers, by the hooded form of the buds and the maintenance of such form until the same open, by the Carmine general color tonality of the flowers, lightly overcast with Spectrum Red, and by the white stripe occurring in and confined to a single petal of each flower near the middle of the flower, substantially as herein shown and described.

WILHELM KORDES.

No references cited.